United States Patent

Suh et al.

[11] Patent Number: 5,634,956
[45] Date of Patent: Jun. 3, 1997

[54] BIOCERAMICS USED IN ARTIFICIAL BONE AND ARTIFICIAL DENTAL IMPLANTS AND THE PROCESS FOR THE PREPARATION THEREOF

[75] Inventors: Chung K. Suh, Seoul; Ho K. Kim, Kyunggi-Do, both of Rep. of Korea

[73] Assignee: Samjo Industrial Co., Ltd., Kyunggi-Do, Rep. of Korea

[21] Appl. No.: 491,681
[22] Filed: Jun. 19, 1995
[51] Int. Cl.$^6$ .......... C03B 27/012; C03B 32/00; C03C 10/00
[52] U.S. Cl. .......... 65/33.1; 65/17.3; 65/33.2; 65/61; 65/63; 65/134.1; 65/144; 433/213; 433/223; 433/228.1; 623/16
[58] Field of Search .......... 65/33.1, 61, 63, 65/33.2, 17.3, 144, 134.1; 501/5, 57, 70, 73; 433/213, 223, 228.1; 623/16

[56] References Cited

U.S. PATENT DOCUMENTS

| | | | |
|---|---|---|---|
| 3,511,609 | 5/1970 | Kato | 65/33.1 |
| 4,113,500 | 9/1978 | Ebihara et al. | 623/16 |
| 4,871,384 | 10/1989 | Kasuga | 65/30.1 |
| 4,906,267 | 3/1990 | Lane et al. | 65/144 |
| 4,906,268 | 3/1990 | Lane et al. | 65/144 |

FOREIGN PATENT DOCUMENTS 8-136147  5/1996  Japan.

OTHER PUBLICATIONS

Hawley, Gessner, G. The Condensed Chemical Dictionary, Tenth Edition, p. 185 1981.

*Primary Examiner*—Donald E. Czaja
*Assistant Examiner*—Michael Philip Colaianni

[57] ABSTRACT

Glass ceramic for use as a biomaterial comprising CaO 34.6 to 54.6%, $SiO_2$ 24.2 to 44.8 %, $P_2O_5$ 0 to 8.0%, $CaF_2$ 0.1 to 1.0% and Mgo 1.0 to 10.0% by weight and characterized by a primary wollastonite crystalline phase ($CaO$, $SiO_2$) and a secondary apatite crystalline phase, and the process for the preparation thereof are disclosed. The glass ceramic of the present invention has superior mechanical properties, good biocompatibility, bioactivity, and no toxicity making it useful as a biomaterial in artificial bone and dental implants.

1 Claim, 1 Drawing Sheet

BIOCERAMICS USED IN ARTIFICIAL BONE AND ARTIFICIAL DENTAL IMPLANTS AND THE PROCESS FOR THE PREPARATION THEREOF

BACKGROUND OF THE INVENTION

1. Field of the Invention

The present invention relates to a bioactive glass ceramic used in artificial bone and dental implants and a process for the preparation thereof.

2. Description of the Prior Art

Extensive research has been conducted to aid the recovery mechanisms of a patient's body which includes a human body. Research has been especially directed to aiding the repair of bone damaged by disease, injury, aging, congenital disease, and the like with artificial materials. Recently, many materials applicable to living tissue have been developed and used.

These materials which are applied to living tissue are referred to as bioactive, and are directly implanted to living tissue in a patient. Bioactive material, or biomaterial, should have good biocompatibility with the patient. Furthermore, some components released by the biomaterial that respond chemically with the patient's body should be nontoxic. Also, after implanted in the body, the biomaterial should not undergo chemical changes that diminish its strength or convert it into toxic material.

Some materials such as metals and high polymers are used as biomaterial in a living body. There are problems associated with the use of metal as a biomaterial, however. These problems include transformation of the metal surface, the solution of metal ions, and poor biocompatibility. High polymers tend to lack sufficient mechanical strength and biocompatibility. Also, monomers dissolved from such a high polymer material can be toxic.

In addition to metals and high polymers, ceramics have been used as biomaterials. Ceramics have demonstrated the advantage of non-toxicity since the components dissolved from ceramics are nontoxic. In particular, $Al_2O_3$ ceramic is not harmful to a patient and has high mechanical strength (1270 MPa of bending strength). Accordingly, $Al_2O_3$ has been used as material for artificial bone and artificial dental implants. However, $Al_2O_3$ ceramic is inactive within a living body, i.e., not bioactive, and thus, cannot chemically bond with bone. Attachment of such an inactive material to living bone requires mechanical joining, e.g., providing a hole in the inactive material so that new bone grows into the hole, thereby joining the bone and inactive material.

To overcede the problems mentioned above, Bioglass® (Hench) has been developed. Bioglass® is a member of the $Na_2O$—$CaO$—$SiO_2$—$P_2O_3$ group of bioactive glass. Although Bioglass® has good biocompatibility, it is not generally utilized because its bending strength is too low (72±25 MPa) to be used alone under load-bearing conditions.

To improve the bending strength of Bioglass®, Ceravital® (Bromer), which is prepared by precipitating the apatite from a glass, and a high density hydroxyapatite ($Ca_{10}(PO_4)_6(OH)_2$) sintered composite (compressive strength: 509 MPa) have been developed. These compositions are capable of chemically bonding with living bone, but have several defects including insufficient mechanical strength and complicated preparation processes.

SUMMARY OF THE INVENTION

It is an object of the present invention to provide biomaterials, apatite-wollastonite glass ceramic of the $SiO_2$—$CaO$—$MgO$—$P_2O_5$ system, having enhanced mechanical strength and good biocompatibility, and the process for preparation thereof.

The glass ceramic of the present invention is a biomaterial which bonds to living bone chemically with calcium phosphate hydrate which may be formed by Ca and P ions dissolved from the biomaterial. The formation of the calcium phosphate hydrate is mediated by Si ion which also dissolved from the material.

The glass ceramic used as a biomaterial of the present invention comprises CaO 34.6 to 54.6%, $SiO_2$ 24.2 to 44.8%, $P_2O_5$ 0 to 8.0%, $CaF_2$ 0.1 to 1.0%, and Mgo 1.0 to 10.0% by weight. The glass ceramic has a primary crystalline phase which is wollastonite ($CaO$, $SiO_2$) and a secondary crystalline phase which can be an apatite.

The glass ceramic of the present invention has overcome the problem of the low mechanical strength of an apatite sintered composite. In the present invention, the strength of the apatite crystal is reinforced by the needle-shaped wollastonite crystal dispersed in the glass matrix. Additionally, apatite-wollastonite glass ceramic has good biocompatibility and can make a strong chemical bond with living bona by the formation of fine apatite crystalline layer between the glass ceramic and living bone. Apatite-wollastonite as a biomaterial can supplement the defects of insufficient biocompatibility and low mechanical strength of artificial bona and dental implant developed thus far.

DETAILED DESCRIPTION OF THE INVENTION

Figure 1:
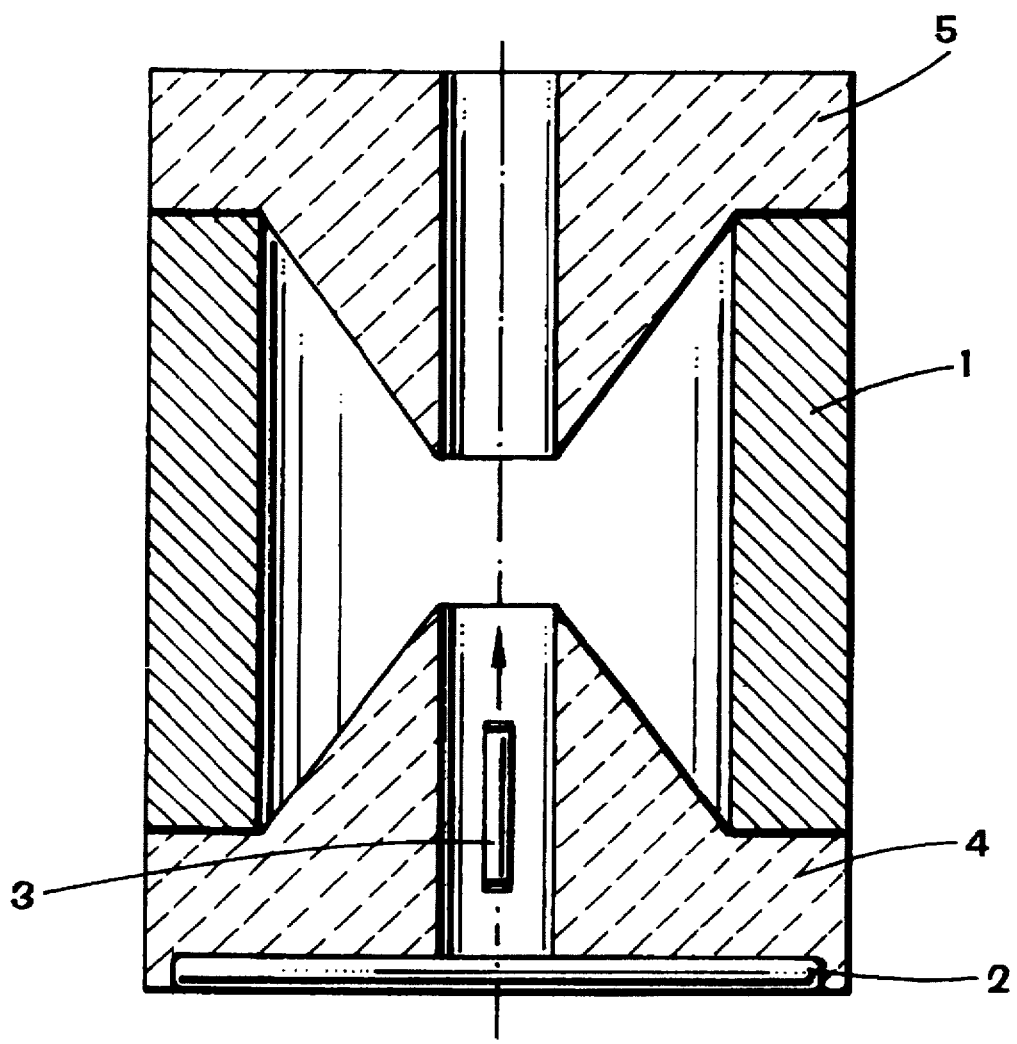
FIG. 1 shows a unidirectional entering furnace used in preparing the bioceramic of the present invention.

Glass ceramic of the present invention was prepared by the process described below.

Calcium phosphate, silica sand, fluorite, calcium carbonate and magnesium oxide were mixed together to produce a mixture with the following proportions: CaO 34.6 to 54.6%, $SiO_2$ 24.2 to 44.8%, $P_2O_5$ 0 to 8.0%, $CaF_2$ 0.1 to 1.0%, and MgO 1.0 to 10.0% by weight. The mixture was placed in a platinum crucible and melted at a temperature ranging from 1450° to 1550° C. The melted mixture was quenched and formed into glass plates. The resulting glass plates were ground into fine glass powder having less than 325 mesh size.

The glass powder was mixed to homogeneity using water as a binder and uniaxially pressed under pressure of about 400 kg/cm². The mixture was then cast into molded products by cold isostatic pressing (CIP) under pressure of about 1400 kg/cm². The molded products 3 were hung on platinum wire in the region of lower refractory 4 of the unidirectional sintering furnace shown in FIG. 1. The temperature of the center of the furnace was elevated to 1000° to 1100° C. by the heating elements 1 and the products were drawn at a speed of 6 to 20 mm/h. The drawing of the product was stopped when the upper end of the products reached the region of the upper refractory 5 of the furnace, and the furnace was slowly cooled by the cooling element 2 to obtain the glass ceramic of the present invention.

The present preparation process of the present invention produces a glass ceramic in which the crystalline structure is highly compact by performing the crystallization under the temperature gradient provided by the specific structure of the unidirectional sintering furnace. In addition, since the procedure for preparing the glass ceramic of the present invention is simple. it is possible to produce the glass ceramic in large quantities at a low cost.

The glass ceramic of the present invention has a hardness of 5.80±0.32 GPa, a compressive strength of 1023±151 MPa and a bending strength of 210 to 240 MPa. An X-ray diffraction analysis and scanning electron microscopy (SEM) observation after soaking the sample in simulated body fluid shows that an apatite layer formed on the surface of the sample. Also, the X-ray diffraction revealed that the glass ceramic sample of the present invention could tightly bond to living bone and is not harmful to the patient.

The present invention is illustrated by the following examples. The examples are presented only for the purpose for illustration and do not limit the scope of the invention.

EXAMPLE 1

Silica sand, calcium carbonate, magnesium oxide and fluorite were mixed in a ratio shown in Table 1 for 24 hours in ball mill. The mixture was calcinated at 1000° C. for 10 hours in a platinum crucible. The resulting calcinated were melted at 1550° C. for 2 hours and quenched while pouring the melted mixture onto a stainless steel plate. The melted mixture was pressed using another stainless steel plate to make a resulting glass having a thickness less than 2 mm.

The resulting glass was pulverized into a fine powder with less than a 325 mesh size (45 μm) by a ball mill crusher. 10 wt % distilled water was added as a binder to the glass powder. The powder was mixed to homogeneity.

The mixture was cast by uniaxially pressing under a pressure of 400 kg/cm$^2$ and heated at 400° C. for 2 hours in the unidirectional furnace to evaporate the binder. The product was cold isostatic pressed under a pressure of about 1400 kg/cm$^2$ (2000 psi). The compressed sample was drawn up at a speed of mm/h at 1050° C. in the unidirectional furnace.

The results of X-ray diffraction analysis on the resulting glass ceramic indicated that the primary crystal phase is wollastonite (CaO, SiO$_2$).

EXAMPLE 2

Calcium phosphate, silica sand and calcium carbonate were mixed in the composition ratio shown in Table 1 using the method described in Example 1. The mixtures were cast and sintered to produce a glass ceramic having an X-ray diffraction pattern showing that the primary crystal phases are apatite and wollastonite.

TABLE 1

| Compositions of glasses (wt %) | | |
|---|---|---|
| Component | Example 1 | Example 2 |
| CaO | 47.9 | 48.6 |
| SiO$_2$ | 44.8 | 44.0 |
| P$_2$O$_5$ | — | 7.4 |
| MgO | 6.3 | — |
| CaF$_2$ | 1.0 | — |

The mechanical properties of the produced glass ceramic was characterized by the method described below.

Bending Strength

The bar-shaped sintered composite produced by the crystallization of glass was polished successively by using #400, #800, #1200, #2000 alumina abrasive powder and polished optically to produce a sample for determining the strength of the glass. The 3-point bending strengths for the glass ceramic the present invention were determined using an instron-type machine (Model 4204, Instron Co.) under a fixed descending speed of load of 0.5 mm/min and a distance between the supporting axes of the sample of 20 mm. The value of the 3-point bending strength was calculated according to the formula below.

Bending strength (MPa)=3pL/2M wherein, p=load (kg)

L=the distance between axes b=width of sample d=thickness of sample

Compressive Strength

Glass ceramic of the bar type (5×5×5 mm$^3$) was prepared and abraded successively by using #400, #800, #1200, #2000 alumina abrasive powder to make the lower and upper surfaces of the sample level and remove any roughness of each surface. The polished sample was loaded into a Material Testing System (MTS) and compressively stressed under a loading rate of 0.5 mm/min. The stressing force applied to the sample was increased over time and the compressive strength of the sample was determined as the pressure (MPa) producing the fracture of the sample.

The mechanical properties of the glass ceramic prepared in Examples 1 and 2 were tested by using the methods described above. The results are shown in Table 2.

TABLE 2

| The Mechanical Properties of Glass Ceramic of the Present Invention | | |
|---|---|---|
| | Bending strength (MPa) | Compressive strength (MPa) |
| Composition 1 | 215 | 1080 |
| Composition 2 | 220–240 | 1160 |

In vitro and in vivo tests were conducted to confirm the suitability of the glass ceramic of the present invention a biomaterial.

In vitro Test

Samples of the obtained glass ceramic were prepared by cutting them into 10×5×2 mm$^2$ plate-shaped samples. Their surfaces were polished with #2000 alumina paste, and washed with acetone and distilled water.

Preparation of the Simulated Body Fluid

NaCl, NaHCO$_3$, KCl, K$_2$HPO$_4$, MgCl$_2$ . 6H$_2$O, CaCl$_2$ and Na$_2$SO$_4$ were dissolved in distilled water, which was passed through an ion exchange resin, to produce a solution having ion concentrations of Na$^+$ 142.0, K$^+$ 5.0, Mg$^{2+}$ 1.5, Ca$^{2+}$ 2.5, Cl$^-$ 147.8, HCO$_3^-$ 4.2, HPO$_4^{2-}$ 1.0, and SO$_4^{2-}$ 0.5 mM.

(CH$_2$OH)$_3$NH$_2$, as a buffering agent, was added to the solution. HCl was added to adjust the pH to 7.28 and the solution was kept at 36.5° C.

The surface microstructure of a glass ceramic sample was observed through X-ray diffraction and SEM observation. samples were analyzed before soaking in the solution, and after the samples had been soaked in 20 ml of the simulated body fluid for 3, 5, and 7 days.

The X-ray diffraction pattern of the sample before soaking revealed that the peak of apatite crystal was mixed with that of wollastonite crystal. After increasing the soaking time, i.e., 3, 5, and 7 days, the peak decreased while that of the apatite crystal increased. These results show that the surface of a glass ceramic sample become gradually coated with the new apatite crystal layer which is formed after soaking.

In Vivo Test

Biocompatibility test (tooth and maxillary bone)

After generally anesthetizing a 3 month old rabbit, a cylindrical hole was introduced in the foretooth of the inferior maxilla and in the maxillary bone with a drill.

The holes were filled with the biomaterial of the present invention. Thereafter, the hole in the tooth was covered with a hardening material using a plugger, and treated with an occluding agent to prevent loss of the biomaterials. The periosteum in the maxillary bone was sutured with the outer layer of the skin.

The rabbits were treated with antibiotics for several days. After 1, 2, and 4 weeks, the tooth and the maxillary bone were removed and subjected to SEM analysis and X-ray radiography.

The results show that the boundary between the biomaterial and living tissue became indistinct, proving that the biomaterial can make a strong chemical bond with living tissue over time.

Determination of biocompatibility and strength (tibia)

After generally anesthetizing New Zealand white rabbits (Oryctolagus cuniculus) (about 2.5 kg in weight), a tibia segment were resected at a point distal to the junction of the tibia and the fibula to induce a bone defect.

The biomaterials were inserted into the bone defect region of the rabbit and sutured. Antibiotics were intramuscularly injected into the hind leg of the rabbit to protect them from post-operational infection.

After sacrificing the rabbits at 2, 4, 8, and 16 weeks, their tibias were removed and observed using radiographs. The radiographs indicated that the radiolucent gap between the tibia and the biomaterial gradually diminished, proving that the biomaterial of the present invention has good compatibility with the tibia.

The four-point bending test on the joint between the living bone and artificial bone shows that the biomaterial of the present invention has a good break strength of about 62%

Toxicity test

The circle plate shaped biomaterials (13 mm×1 mm) of the present invention was cultured with $1.25 \times 10^6$ L929 fibroblast in a plastic dish used for tissue culture, in a culture medium comprising 10% horse plasma (Gibco U.S.A.), penicillin (100 unit/ml), streptomycin (100 unit/ml) and a minimal medium, e.g., Eagle's solution (BME: Gibco, U.S.A.), to which fungizone (0.3 μm/ml) is added.

Cultivation was carried out in an incubator (Precision, U.S.A.) at 37° C., 90% humidity, and an air composition of 5% $CO_2$ and 95% air. After culturing for 24 hours, 3 ml of 1.5% agar (Difco, U.S.A.)/BME solution was poured into the dish to form the agar layer on the cellular layer. Neutral red solution (0.01%) was used to stain the tissue culture.

The degree of decoloration and cell lysis of the stained cells were examined with an unaided eye and under a microscope. No discoloration around and under the biomaterials was found and no cell lysis occurred. Thus, the biomaterials of the present invention are non-toxic.

The tests described above confirm that the glass ceramic of the present invention has excellent mechanical strength, good bioactivity and biocompatibility, and is nontoxic. Thus, it is useful as a biomaterial for artificial bone and artificial dental implants.

The present invention is described based on the examples above. However, it should not be regarded as being limited by them, and persons who have ordinary skill in the relevant technical field can modify the present invention within the scope of the claims.

What is claimed is:

1. A process for preparing a biocompatible glass ceramic, comprising the steps of:

mixing calcium phosphate, silica sand, fluorite, calcium carbonate, and magnesium oxide to produce a mixture having the following proportions: CaO 34.6 to 54.6%, $SiO_2$ 24.2 to 44.8%, $P_2O_5$ 0 to 8.0%, $CaF_2$ 0.1 to 1.0% and MgO 1.0 to 10% by weight;

melting said mixture at a temperature ranging from 1440° to 1550° C. to produce a melt;

quenching said melt;

grinding the quenched melt to produce a glass powder particles having less than 325 mesh size;

pressing said glass powder particles by cold isostatic pressing to produce a molded product; and crystallizing the molded product in a unidirectional sintering furnace having a center temperature of 1800° to 1100° C. while drawing the molded product at a speed of 6 to 20 mm/hr until the upper end of said product reaches the upper portion of the furnace then gradually cooling the furnace.

* * * * *

UNITED STATES PATENT AND TRADEMARK OFFICE
CERTIFICATE OF CORRECTION

PATENT NO. : 5,634,956
DATED      : June 3, 1997
INVENTOR(S) : Chung K. Suh, Ho K. Kim It is certified that error appears in the above-indentified patent and that said Letters Patent is hereby corrected as shown below:

Col. 1, line 32, delete "solution" and insert -- elution --.
Col. 2, line 23, delete "bona" and insert -- bone --.
Col. 2, line 27, delete "bona" and insert -- bone --.
Col. 2, line 31, delete "entering" and insert -- sintering --.
Col. 3, line 36, insert -- 6 -- after the word of.
Col. 4, line 10, delete "/2M" and insert -- /2bd --.
Col. 4, line 61, delete "7.28" and insert -- 7.25 --.
Col. 4, line 65, delete "samples" and insert -- Samples --.
Col. 5, line 4, insert --of wollastonite crystal-- after the word peak.
Col. 6, line 45, delete "1800°" and insert -- 1000° --.

Signed and Sealed this

Seventh Day of October, 1997

Attest:

BRUCE LEHMAN

*Attesting Officer*     *Commissioner of Patents and Trademarks*